United States Patent
Ogawa

(10) Patent No.: US 11,523,062 B2
(45) Date of Patent: Dec. 6, 2022

(54) IMAGE CAPTURE APPARATUS AND METHOD FOR CONTROLLING THE SAME

(71) Applicant: CANON KABUSHIKI KAISHA, Tokyo (JP)

(72) Inventor: Shigeo Ogawa, Yokohama (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 17/484,328

(22) Filed: Sep. 24, 2021

(65) Prior Publication Data

US 2022/0014685 A1   Jan. 13, 2022

Related U.S. Application Data

(63) Continuation of application No. 16/276,012, filed on Feb. 14, 2019, now Pat. No. 11,165,964.

(30) Foreign Application Priority Data

Feb. 20, 2018   (JP) .............................. JP2018-027816

(51) Int. Cl.
*H04N 5/232* (2006.01)
*H04N 5/77* (2006.01)
(Continued)

(52) U.S. Cl.
CPC ..... *H04N 5/232939* (2018.08); *A61B 5/7495* (2013.01); *A61B 90/96* (2016.02); *H04N 1/00334* (2013.01); *H04N 1/2112* (2013.01); *H04N 1/32106* (2013.01); *H04N 1/32128* (2013.01); *H04N 5/23218* (2018.08); *H04N 5/23241* (2013.01); *H04N 5/232935* (2018.08); *H04N 5/232941* (2018.08); *H04N 5/772* (2013.01); *H04N 2101/00* (2013.01); *H04N 2201/0084* (2013.01);
(Continued)

(58) Field of Classification Search
CPC ....... H04N 1/00334; H04N 2201/3276; H04N 2201/3277; H04N 5/23241; H04N 5/23218; H04N 5/23219; H04N 5/232935; H04N 5/232939; H04N 5/232941; A61B 5/7495; A61B 90/96
See application file for complete search history.

(56) References Cited

U.S. PATENT DOCUMENTS

| | | | |
|---|---|---|---|
| 6,393,431 B1 * | 5/2002 | Salvati | A61B 1/00052 |
| 11,165,964 B2 * | 11/2021 | Ogawa | H04N 5/232941 |

FOREIGN PATENT DOCUMENTS

| | | |
|---|---|---|
| JP | S63-044217 A | 2/1988 |
| JP | 2002-230182 A | 8/2002 |

(Continued)

*Primary Examiner* — Daniel M Pasiewicz
(74) *Attorney, Agent, or Firm* — Canon U.S.A., Inc. IP Division

(57) ABSTRACT

An image capture apparatus displays a live view image that is based on an acquired image, stores image data that is based on the acquired image, and acquires additional information associated with a predetermined subject included in the live view image. The image capture apparatus superimposes the additional information on the live view image and displays the resulting image before the image data is stored, and stores the image data and the acquired additional information in association with each other.

15 Claims, 7 Drawing Sheets

(51) Int. Cl.
*H04N 1/21* (2006.01)
*H04N 1/32* (2006.01)
*A61B 5/00* (2006.01)
*H04N 1/00* (2006.01)
*A61B 90/96* (2016.01)
*H04N 101/00* (2006.01)

(52) U.S. Cl.
CPC ............... *H04N 2201/3269* (2013.01); *H04N 2201/3276* (2013.01); *H04N 2201/3277* (2013.01)

(56) References Cited

FOREIGN PATENT DOCUMENTS

| | | |
|---|---|---|
| JP | 2003-052767 A | 2/2003 |
| JP | 2009-130688 A | 6/2009 |
| JP | 2012-010358 A | 1/2012 |
| JP | 2014-236284 A | 12/2014 |
| WO | 2006/035788 A1 | 4/2006 |

\* cited by examiner

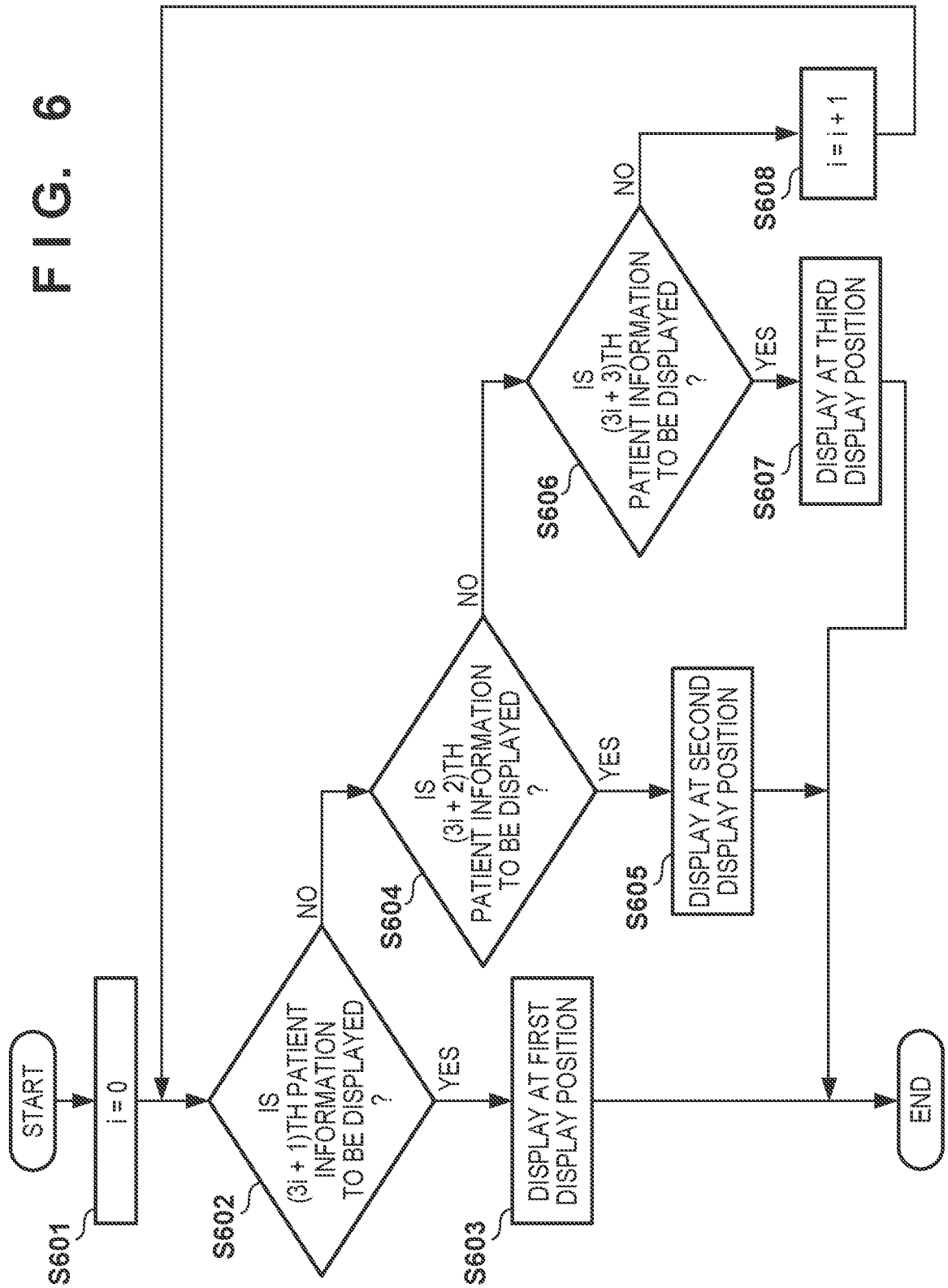

IMAGE CAPTURE APPARATUS AND METHOD FOR CONTROLLING THE SAME

CROSS-REFERENCE TO RELATED APPLICATION

This application is a Continuation of U.S. application Ser. No. 16/276,012, filed Feb. 14, 2019, which claims priority from Japanese Patent Application No. 2018-027816, filed Feb. 20, 2018, which are hereby incorporated by reference herein in their entireties.

BACKGROUND

Field

The present disclosure relates to an image capture apparatus and a method for controlling the same.

Description of the Related Art

Technology for associating a given subject appearing in an image with information regarding the subject has been proposed. For example, Japanese Patent Laid-Open No. 2003-52767 discloses a system that outputs a sheet on which a picture of a patient and a barcode indicating the identification number of this patient are displayed in association with each other. Also, Japanese Patent Laid-Open No. 2002-230182 discloses a system that downloads a picture of a patient from a database based on ID information read out from a barcode attached to a wristband of the patient, and displays the picture on the screen of a terminal.

It is conceivable that an image capture apparatus configured to record an obtained image of a subject in association with information regarding the subject is configured as one aspect for associating a subject and information regarding the subject. For example, a barcode or the like associated with the information regarding the subject is read out and information regarding the subject is acquired in advance, and, when the obtained image data of the subject is recorded, the acquired information regarding the subject can be associated with the image data.

However, in a case where, when an image is obtained, a photographer cannot specify the information regarding the subject acquired in advance, there has been the risk that information irrelevant to the subject appearing in the obtained image will be erroneously associated with the obtained image data.

SUMMARY

The present disclosure has been made in consideration of the aforementioned, and realizes a technique with which, when an obtained image and information regarding a subject are recorded in association with each other, the subject and information are prevented from being erroneously associated with each other.

The present disclosure provides an image capture apparatus comprising an image capture unit, a display control unit configured to perform control to display, on a display unit, a live view image that is based on an image acquired by the image capture unit, a recording unit configured to record, in a recording medium, image data that is based on the acquired image, and an information acquisition unit configured to acquire additional information associated with a predetermined subject included in the live view image, wherein the display control unit performs control to superimpose the acquired additional information on the live view image and display a resulting image on the display unit before the image data is recorded in the recording medium, and wherein the recording unit records the image data and the acquired additional information in the recording medium in association with each other.

The present disclosure provides a method of controlling an image capture apparatus, the method comprising displaying a live view image that is based on an acquired image, storing image data that is based on the acquired image acquired, acquiring additional information associated with a predetermined subject included in the live view image, superimposing the acquired additional information on the live view image, and displaying a resulting image before the image data is stored, wherein the image data and the acquired additional information are stored in association with each other.

The present disclosure provides a non-transitory computer-readable storage medium storing a program that, when executed by a processor, causes the processor to perform operations comprising displaying a live view image that is based on an acquired image, storing image data that is based on the acquired image, acquiring additional information associated with a predetermined subject included in the live view image, superimposing the additional information on the live view image, and displaying a resulting image before the image data is stored, wherein the image data and the acquired additional information are stored in association with each other.

According to the present disclosure, when an obtained image and information regarding a subject are recorded in association with each other, it is possible to prevent the subject and information from being erroneously associated with each other.

Further features will become apparent from the following description of exemplary embodiments with reference to the attached drawings.

BRIEF DESCRIPTION OF THE DRAWINGS

FIG. 6 is a flowchart illustrating one example of processing for displaying patient information in the image capture apparatus according to an embodiment.

DESCRIPTION OF THE EMBODIMENTS

An image capture apparatus, a method for controlling the image capture apparatus, and a recording medium in which a program is stored according to the present embodiment will be described with reference to FIGS. 1 to 7A to 7C.

Figure 1:
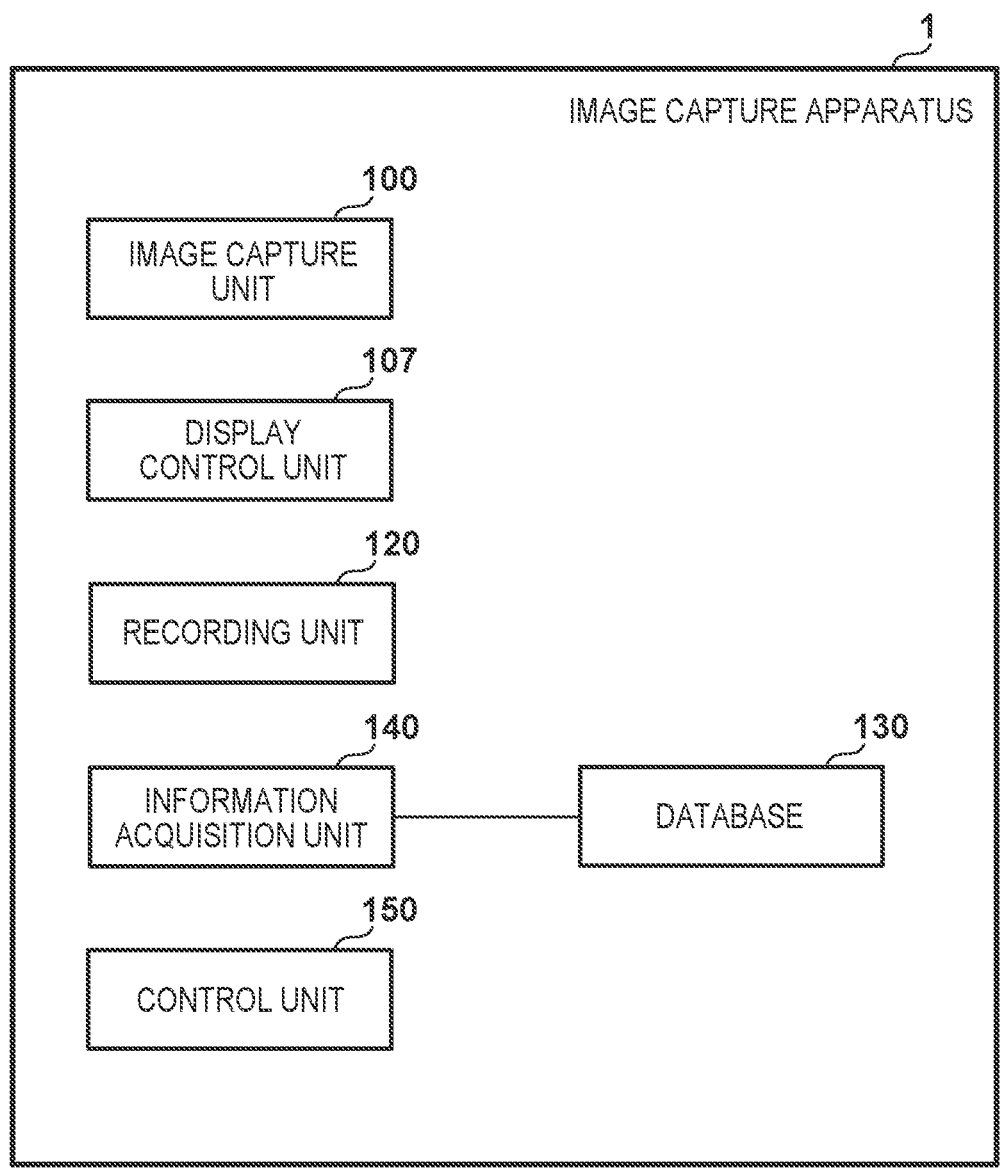
FIG. 1 is a block diagram illustrating a functional configuration of an image capture apparatus according to an embodiment.
Figure 2:
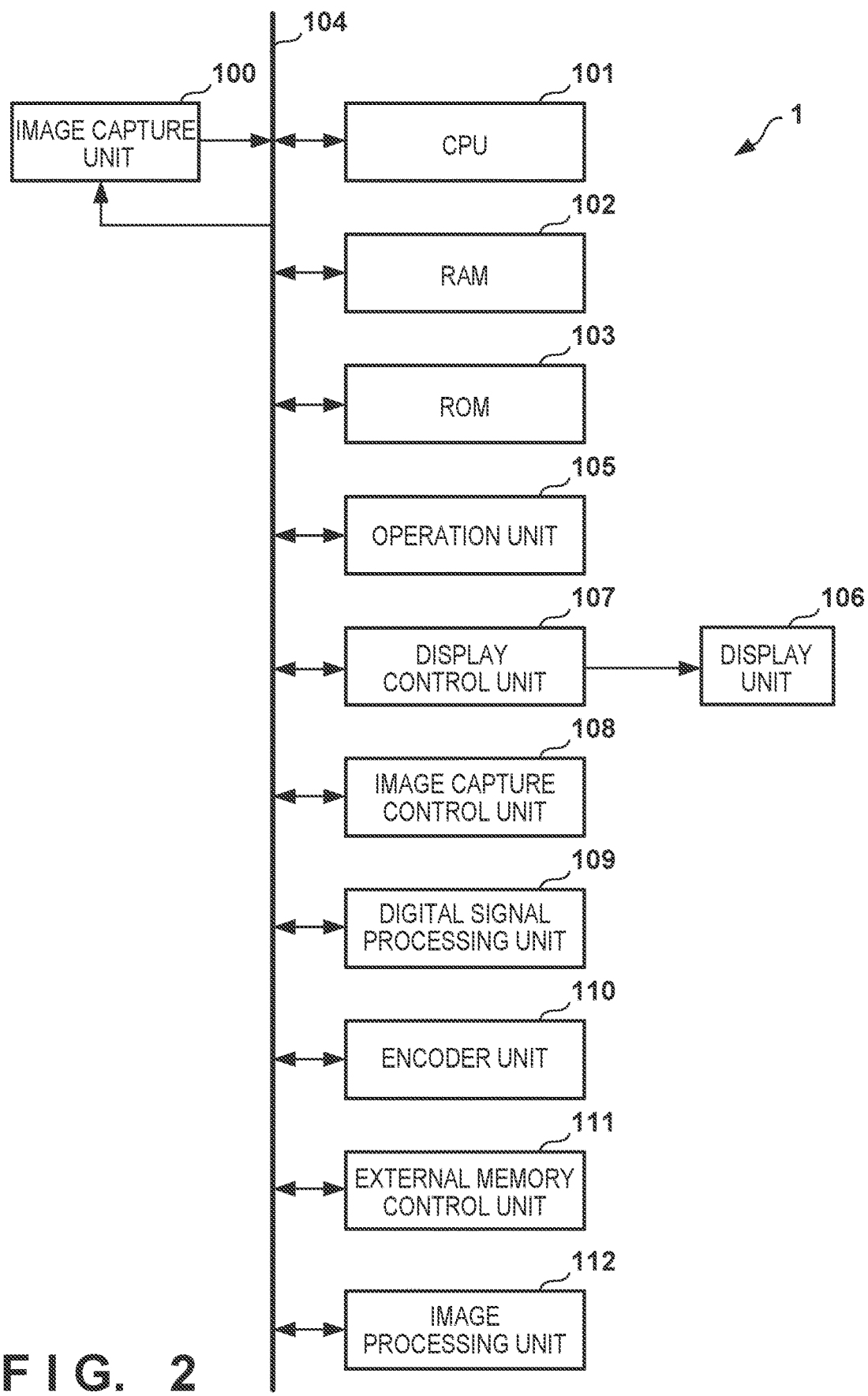
FIG. 2 is a block diagram illustrating a hardware configuration of the image capture apparatus according to an embodiment.

First, a schematic configuration of an image capture apparatus that realizes an electronic device in the present embodiment will be described with reference to FIGS. 1 and 2. FIG. 1 is a block diagram illustrating a functional configuration of the image capture apparatus according to the present embodiment. FIG. 2 is a block diagram illustrating a hardware configuration of the image capture apparatus according to the present embodiment.

As illustrated in FIG. 1, an image capture apparatus 1 according to the present embodiment includes an image capture unit 100, a display control unit 107, a recording unit 120, a database 130, an information acquisition unit 140, and a control unit 150.

The image capture unit 100 is a camera unit that converts an optical image of a subject into an electrical signal and outputs an image. Still image data or moving image data is generated as a result of executing compression coding processing or the like on an image. The image capture unit 100 includes an image sensor constituted by a CCD image sensor, a CMOS image sensor, or the like. The image capture unit 100 can include an A/D conversion unit configured to convert an analog signal output from the image sensor into a digital signal. Note that the image capture unit 100 can be located external to the image capture apparatus 1 and acquire an image from an external image capture unit 100 via a communication unit of the image capture apparatus 1.

The database 130 stores a look up table for associating each of a plurality of codes with predetermined additional information (patient information in the present embodiment). A "code" is a one-dimensional code such as a barcode or a two-dimensional code such as a QR Code®, and is an identifier in which numerical values or letters are expressed using a figure. The look up table is for associating patient information with numerical values or letters read from a code. An example of the code is a barcode attached to a wristband worn by a patient, and patient information associated with a barcode includes the ID number or name of the patient. Note that the database 130 can be located external to the image capture apparatus 1, and the information acquisition unit 140 can search the database 130 via a network or a communication line, and acquire patient information.

The information acquisition unit 140 has the functions of searching the database 130 based on the numerical values or letters read from a code appearing in the image acquired by the image capture unit 100, and acquiring the patient information associated with this code from the database 130.

The display control unit 107 includes the function of performing control to display an image that is based on the image data acquired by the image capture unit 100 on the display unit 106 (see FIG. 2). The display control unit 107 also includes the function of performing control to superimpose the patient information acquired by the information acquisition unit 140 from the database 130 on an image that is based on the image data acquired by the image capture unit 100 and display the resulting image on the display unit 106. Note that the image data acquired by the image capture unit 100 is also utilized in a function for displaying an image that is based on the image data acquired by the image capture unit 100 on the display unit 106 in real-time, that is, a so-called live view function.

The recording unit 120 includes the function of recording the image data acquired by the image capture unit 100 in a recording medium (not shown). The recording medium is a flash memory or the like, for example, and can be attachable to and detachable from the image capture apparatus. The recording unit 120 also includes the function of recording the image data acquired by the image capture unit 100 and the patient information acquired by the information acquisition unit 140 from the database 130 in association with each other. Note that there is no particular limitation on a mode in which the image data acquired by the image capture unit 100 and the patient information acquired by the information acquisition unit 140 from the database 130 are recoded in association with each other. For example, a method for recording, as one file, image data to which information data has been added, or a method for recording image data and patient information data as separate files that are associated with each other using file names or the like can be used.

The control unit 150 includes the function of performing overall control of the image capture unit 100, the display control unit 107, the recording unit 120, and the information acquisition unit 140.

The functions of the image capture apparatus illustrated in FIG. 1 can be realized by a hardware configuration shown in FIG. 2, for example.

As illustrated in FIG. 2, the image capture apparatus 1 according to the present embodiment includes the image capture unit 100, a CPU (central processing unit) 101, a RAM 102, a ROM 103, a bus 104, an operation unit 105, the display unit 106, and the display control unit 107. The image capture apparatus 1 includes an image capture control unit 108, a digital signal processing unit 109, an encoder unit 110, an external memory control unit 111, and an image processing unit 112. These units are communicably connected to each other via the bus 104.

As described above, the image capture unit 100 is a camera unit that converts an optical image of a subject into an electrical signal and outputs the converted electrical signal as image data.

The CPU 101 is a processor that collectively controls constituent components of the image capture apparatus 1. The CPU 101 includes the function of the control unit 150. The RAM 102 is a memory functioning as a main memory, a work area, or the like of the CPU 101. The ROM 103 is a memory for storing a control program or the like executed by the CPU 101. The bus 104 is a transmission path for various kinds of data. For example, the image data acquired by the image capture unit 100 is transmitted to a predetermined processing unit via the bus 104.

The operation unit 105 is a device for the user (photographer) to input an instruction to the image capture apparatus 1. The operation unit 105 is constituted by a power source button, a shutter button, and a mode dial, for example. The mode dial is a dial for switching operation modes such as an information acquisition mode and a shooting mode, for example.

The display unit 106 is a display device that displays an image, letters, or the like, and is constituted by a liquid crystal display or the like, for example. The display unit 106 can also include a touch input function as a touch screen, and, in this case, the touch screen also corresponds to the operation unit 105. If the image capture apparatus 1 has a finder, the finder also corresponds to the display unit 106.

The display control unit 107 is an interface for controlling the displaying of an image, letters, or the like displayed on the display unit 106.

The image capture control unit 108 controls the image capture unit 100 based on an instruction issued from the CPU 101, through focus adjustment, shutter opening or closing, and aperture diaphragm adjustment, etc.

The digital signal processing unit 109 performs, on the image data received via the bus 104, image processing such as white balance processing, gamma processing, and noise reduction processing, for example.

The encoder unit 110 performs processing for converting the image data received via the bus 104 into a file format such as JPEG or MPEG, for example.

The external memory control unit 111 is an interface for connecting the image capture apparatus 1 to a PC or a recording medium (for example, a hard disk, a memory card, a CF card, an SD card, a USB memory, or the like). The image data acquired by the image capture unit 100 and the image data generated by the image processing unit 112 are recorded in a recording medium (not shown) via the external memory control unit 111. That is, the external memory control unit 111 includes the function of the recording unit 120.

The image processing unit 112 performs image processing such as generation of a display image, using the image data acquired by the image capture unit 100 or the image data output by the digital signal processing unit 109. Also, the image processing unit 112 analyzes a code appearing in the image acquired by the image capture unit 100. That is, the image processing unit 112 includes the function of the information acquisition unit 140.

Next, basic operations of the image capture apparatus according to the present embodiment will be described.

The image capture apparatus 1 includes an information acquisition mode and a shooting mode as operation modes. The information acquisition mode is a mode in which patient information associated with a code is acquired from the database 130 based on the code obtained by the image capture apparatus 1. The shooting mode is a mode in which image data of a subject is acquired. The operation mode can be selected via an operation made by a photographer via the operation unit 105. Note that a transition from the information acquisition mode to the shooting mode can automatically occur in response to completion of acquisition of patient information in the information acquisition mode.

Figure 3:
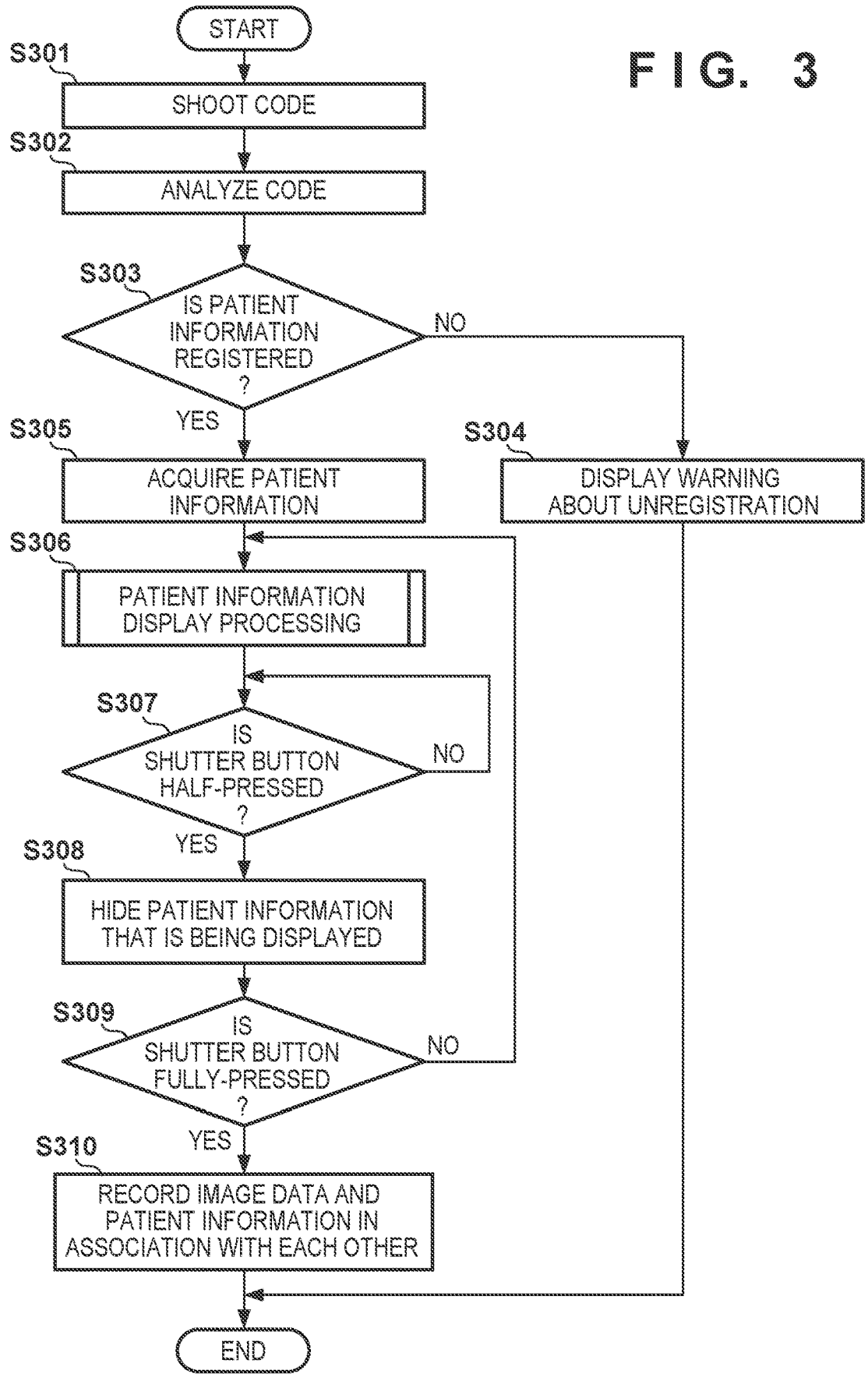
FIG. 3 is a flowchart illustrating an example of basic operations of the image capture apparatus according to an embodiment.

FIG. 3 is a flowchart illustrating an example of basic operations of the image capture apparatus according to the present embodiment. In the process from step S301 to step S310 illustrated in FIG. 3, the process from step S301 to step S305 corresponds to operations in the information acquisition mode, and the process from step S306 to step S310 corresponds to operations in the shooting mode.

First, in step S301, the image capture unit 100 shoots an image of a code in response to an operation made by the photographer via the operation unit 105. Herein, a case where a code is a barcode attached to a wristband worn by a patient is presumed as one example.

Next, in step S302, the information acquisition unit 140 reads and analyzes the code appearing in the image acquired by the image capture unit 100 using a predetermined analysis method, and acquires character strings indicated by the code.

Next, in step S303, the information acquisition unit 140 searches the database 130 based on the result of analysis of the code appearing in the image acquired by the image capture unit 100, and determines whether patient information associated with this code is registered in the database 130. In the above-described example, the patient information registered in the database 130 includes the ID number or name of a patient associated with information indicated by the barcode, for example. Note that the information indicated by the barcode can be the ID number of the patient, the name or the like of the patient can be registered in the database 130, and the database 130 can be searched for the name of the patient based on the ID number.

As a result of searching the database 130, if the information associated with the code appearing in the image acquired by the image capture unit 100 is not registered in the database 130 ("NO" in step S303), the process proceeds to step S304. Then, in step S304, the display control unit 107 displays a warning message indicating that the patient information associated with the code appearing in the image acquired by the image capture unit 100 is not registered in the database 130 superimposed on a live view image displayed on the display unit 106.

Figure 4A:
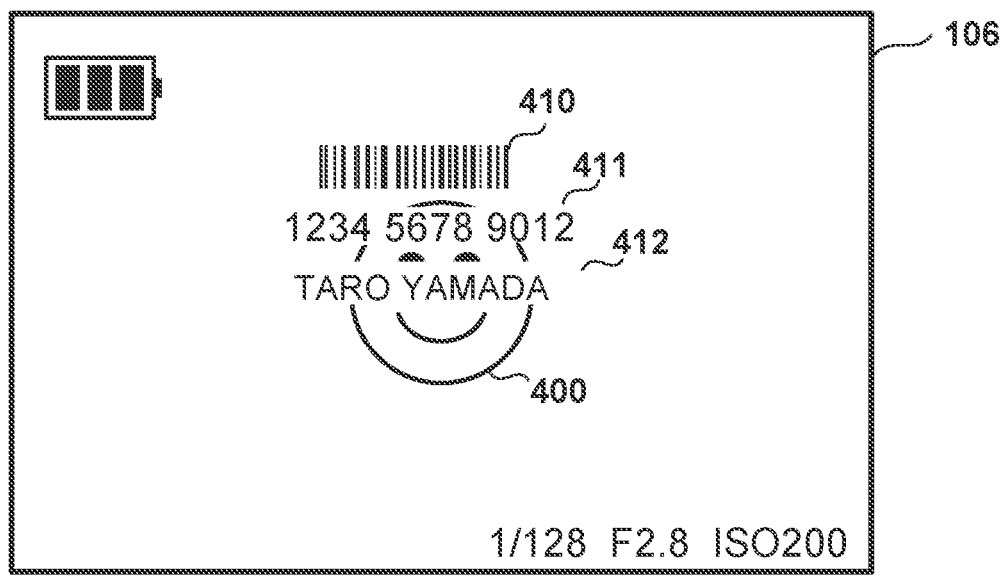
FIGS. 4A and 4B are diagrams illustrating display examples of patient information and a warning message in the image capture apparatus according to an embodiment.
Figure 4B:
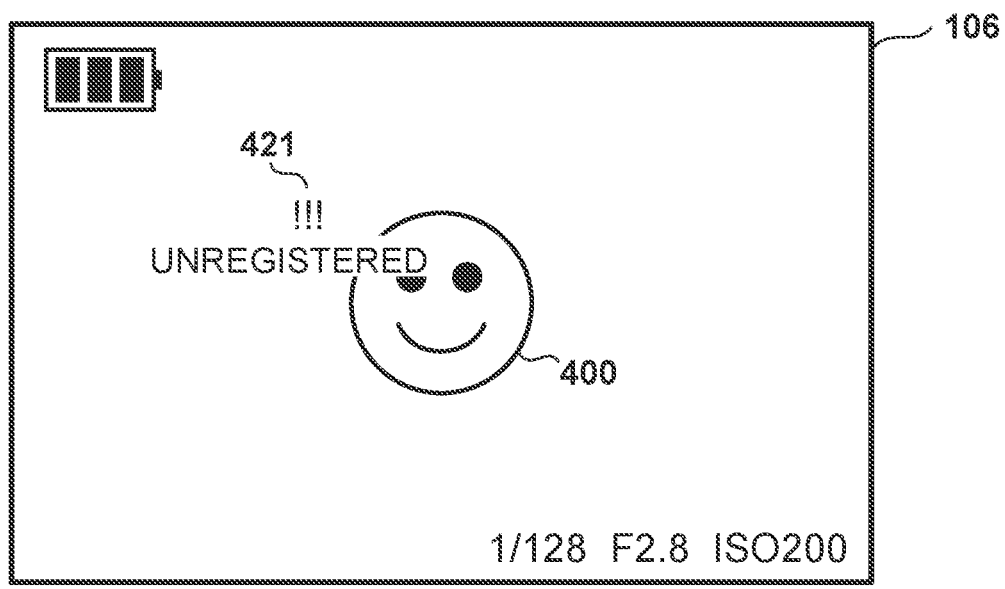

FIG. 4B is a diagram illustrating one example of a warning message displayed on the display unit 106. If the patient information associated with the code appearing in the image acquired by the image capturing unit 100 is not registered in the database 130, the display control unit 107 displays a warning message 421 as illustrated in FIG. 4B, superimposed on a live view image 400. Note that, if the information associated with the obtained code is not registered in the database 130, acceptance of a shooting instruction in the shooting mode can be prohibited.

As a result of searching the database 130, if the patient information associated with the code appearing in the image acquired by the image capture unit 100 is registered in the database 130 ("YES" in step S303), the process proceeds to step S305. Then, in step S305, the information acquisition unit 140 acquires the patient information associated with the code appearing in the image acquired by the image capture unit 100 from the database 130.

A subject associated with the code obtained in the information acquisition mode is obtained in the shooting mode. In the above-described example, the subject is a patient wearing a wristband to which the barcode is attached.

Next, in step S306, the display control unit 107 displays the patient information acquired by the information acquisition unit 140 from the database 130 superimposed on the live view image displayed on the display unit 106 until a shooting instruction to capture an image of a subject is issued in the shooting mode. By displaying the patient information superimposed on the live view image, the photographer can grasp, at a glance, patient information scheduled to be recorded in association with the data of an image of a subject to be obtained. For example, if there is an error, such as patient information still being the patient information regarding the previous subject due to a failure in obtaining an image of a code or acquiring different patient information by erroneously reading a code, the photographer can easily notice that the subject in the live view image does not coincide with the patient information. The photographer then captures an image of the code of the wristband worn by the subject again, and the above-described process from step S301 is performed again, and thus the photographer can change the patient information to correct patient information. Thus, it is possible to prevent a subject and patient information from being erroneously associated with each other. Note that patient information can be displayed on the display unit 106 continuously or intermittently.

FIG. 4A is a diagram illustrating one example of patient information displayed on the display unit 106. If patient information associated with the code obtained in the information acquisition mode is registered in the database 130, the display control unit 107 displays patient information as illustrated in FIG. 4A superimposed on the live view image 400. The code in this example is a barcode attached to a wristband worn by a patient, and patient information associated with the barcode includes the ID number and name of this patient, for example. Note that, while a thumbnail image 410 of the barcode obtained in the information acquisition mode, an ID number 411 of a patient, and a name 412 of the patient are displayed on the display unit 106 in FIG. 4A, the thumbnail image 410 of the barcode may not be displayed.

Next, the control unit 150 determines in step S307 whether a shutter button is half-pressed by the photographer. If it is determined that the shutter button is half-pressed ("YES" in step S307), the process proceeds to step S308. If it is determined that the shutter button is not half-pressed ("NO" in step S307), the patient information remains displayed on the display unit 106, and the process returns to step S307. Note that the control unit 150 detects an operation made by the photographer on the shutter button in two stages that are a half-press and a full-press.

Next, in step S308, the display control unit 107 hides the patient information displayed on the display unit 106. It is conceivable that half-pressing of the shutter button is an operation indicating that the photographer has decided a subject whose image is to be obtained, that is, an instruction to start image capturing is issued. As a result of hiding the patient information, the photographer can more easily check, on the display unit 106, a subject whose image is to be obtained without patient information being in the way. Note that, while the patient information is hidden if it is determined that the shutter button is half-pressed in the present embodiment, a configuration can be adopted in which patient information is hidden as a result of detecting that another operation member has been operated instead of the shutter button. Also, a configuration can be adopted in which the patient information is hidden if a predetermined time period has elapsed after patient information is displayed.

Next, the control unit 150 determines in step S309 whether the shutter button is fully-pressed by the photographer and a recording instruction to record an obtained image of the subject has been issued. If it is determined that the recording instruction to record the obtained image of the subject has been issued ("YES" in step S309), the process proceeds to step S310. If it is determined that the recording instruction to record the obtained image of the subject has not been issued ("NO" in step S309), the process returns to step S306, and the display control unit 107 displays the patient information superimposed on the live view image displayed on the display unit 106 again. If a shutter button pressing operation is cancelled or a pressing operation is not detected due to the photographer not completing half-pressing, for example, the control unit 150 determines that the recording instruction to record the obtained image of the subject has not been issued.

Next, in step S310, in response to the fact that full-pressing of the shutter button has been detected, the recording unit 120 records the image data of the subject acquired by the image capture unit 100 in a recording medium in association with the patient information acquired by the information acquisition unit 140 from the database 130.

The patient information acquired from the database 130 in step S305 based on the code obtained in the information acquisition mode is temporarily stored in a memory, such as the RAM 102, as information scheduled to be recorded in association with image data of the subject acquired in the shooting mode. When patient information is displayed in step S306, the patient information stored in this memory is read out, and displayed on the display unit 106 together with the live view image. When the image data of the subject is recoded in step S310, the patient information stored in this memory is read out as patient information recorded in association with the image data of the subject. The patient information stored in the memory is rewritten each time the process from step S301 to S305 is executed in the information acquisition mode and new patient information is acquired.

A configuration can be adopted in which patient information stored in the memory is optionally deleted through an operation made by the photographer. Patient information stored in the memory can be deleted in conjunction with turning off a power source of the image capture apparatus 1. For example, a configuration can be adopted in which, when the power source of the image capture apparatus 1 is turned off, patient information stored in the memory is automatically deleted per a setting made by the photographer. A configuration can be adopted in which, by asking, when turning off the power source of the image capture apparatus 1, the photographer whether to delete patient information stored in the memory, the photographer can select whether patient information stored in the memory is to be deleted or stored after the power source is turned off.

Figure 5:
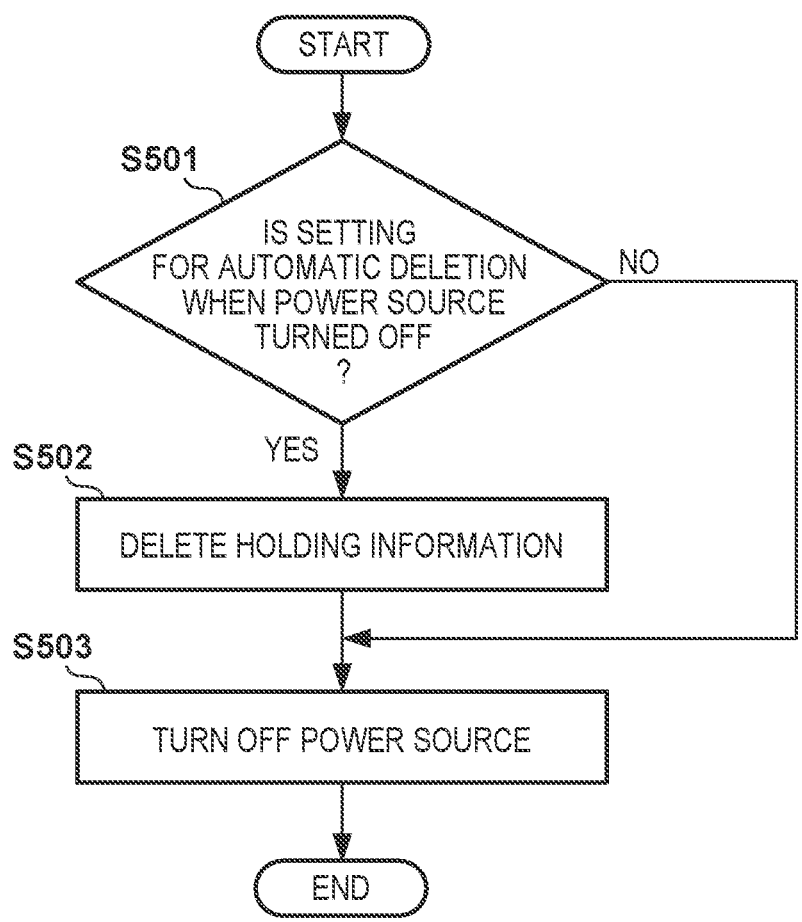
FIG. 5 is a flowchart illustrating one example of processing for deleting patient information when a power source of the image capture apparatus according to this embodiment is turned off.

FIG. 5 is a flowchart illustrating one example of processing for deleting patient information when the power source of the image capture apparatus is turned off.

First, the control unit 150 determines in step S501 whether a setting has been made to automatically delete patient information stored in the memory when the power source is turned off in response to an operation made by the photographer via the operation unit 105.

As a result of the determination, if a setting has been made to automatically delete patient information ("YES" in step S501), the process proceeds to step S502. In step S502, the control unit 150 then deletes patient information stored in the memory. Then, the process proceeds to step S503. If no setting has been made to automatically delete patient information ("NO" in step S501), the process proceeds to step S503 without deleting patient information stored in the memory.

Next, in step S503, the control unit 150 turns off the power source of the image capture apparatus 1 based on a predetermined shutdown sequence. At this time, if patient information is stored in the memory ("NO" in step S501), predetermined processing for keeping the patient information stored in the memory from being lost due to the power source being turned off is performed as needed, such as moving the patient information into a non-volatile memory or the like, for example.

If patient information is stored when the image capture apparatus 1 is turned on, the patient information stored therein can be immediately displayed on the display unit 106.

Next, processing for displaying patient information according to the present embodiment will be described.

The image capture apparatus 1 displays the acquired patient information superimposed on a live view image in the patient information display processing in step S306 shown in FIG. 3. At this time, if the image capture apparatus 1 acquires patient information again, the image capture apparatus 1 can change the position at which the patient information acquired again is displayed. By changing the patient information display position, it is possible to improve the visibility that the displayed patient information has been changed. Note that in order to improve the visibility that the displayed patient information has been changed, instead of changing the patient information display position, the display color can be changed, or the patient information display position and the display color can be changed together.

FIG. 6 is a flowchart illustrating one example of processing for displaying patient information in the image capture apparatus according to this embodiment. In FIG. 6, a case where the display unit 106 has three positions at which patient information is displayed will be described.

First, in step S601, the control unit 150 sets a counter variable i to 0. The control unit 150 sets the counter variable i to 0 if the information acquisition unit 140 acquires patient information, or if it is determined that the stored patient information is to be initially displayed when the image capture apparatus 1 is turned on, for example. Hereinafter, a case where the image capture apparatus 1 is turned on will be described as one example.

Next, in step S602, the control unit 150 determines whether patient information is to be displayed as (3i+1)th patient information after the image capture apparatus is turned on.

Figure 7A:
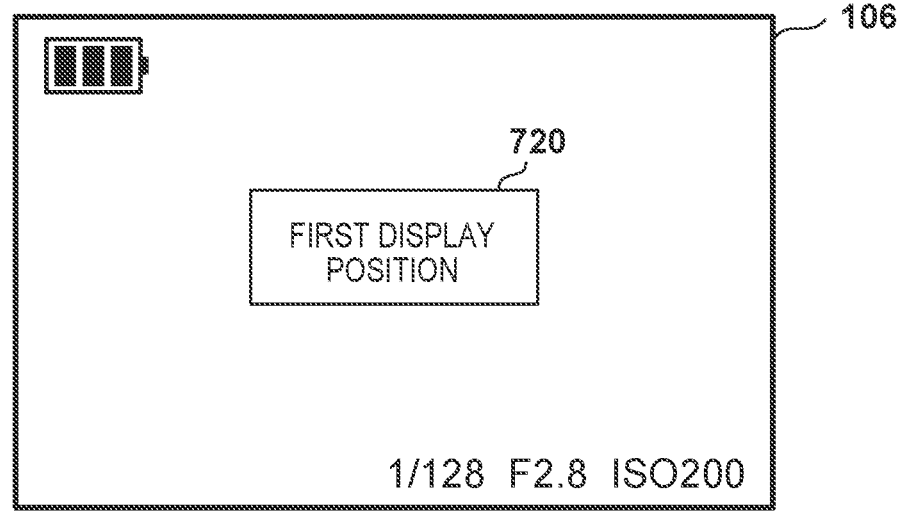
FIGS. 7A to 7C are diagrams illustrating examples for changing a position at which patient information is displayed in the image capture apparatus according to an embodiment.

If it is determined that the patient information is to be displayed as (3i+1)th patient information after the image capture apparatus 1 is turned on ("YES" in step S602), the process proceeds to step S603. In step S603, the display control unit 107 then displays the patient information at a first display position 720 on the display unit 106. FIG. 7A is a diagram illustrating one example of the first display position 720 on the display unit 106 at which the patient information is displayed.

If it is determined that the patient information is not to be displayed as (3i+1)th patient information after the image capture apparatus 1 is turned on ("NO" in step S602), the process proceeds to step S604. The control unit 150 then determines in step S604 whether the patient information is to be displayed as (3i+2)th patient information after the image capture apparatus 1 is turned on.

Figure 7B:
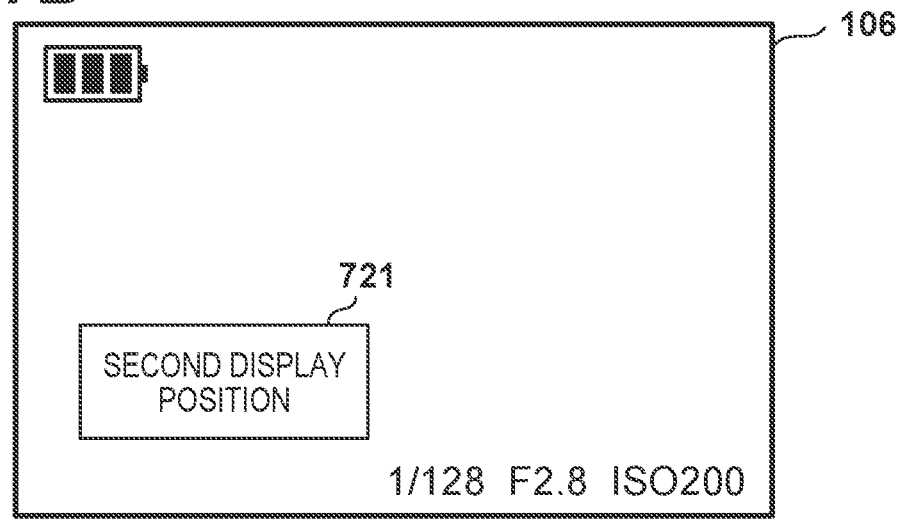

If it is determined that the patient information is to be displayed as (3i+2)th patient information after the image capture apparatus 1 is turned on ("YES" in step S604), the process proceeds to step S605. In step S605, the display control unit 107 then displays the patient information at a second display position 721 on the display unit 106 that is different from the first display position 720. FIG. 7B is a diagram illustrating one example of the second display position 721 on the display unit 106 at which the patient information is displayed.

If it is determined that the patient information is not to be displayed as (3i+2)th patient information after the image capture apparatus 1 is turned on ("NO" in step S604), the process proceeds to step S606. The control unit 150 then determines in step S606 whether the patient information is to be displayed as the (3i+3)th patient information after the image capture apparatus 1 is turned on.

Figure 7C:
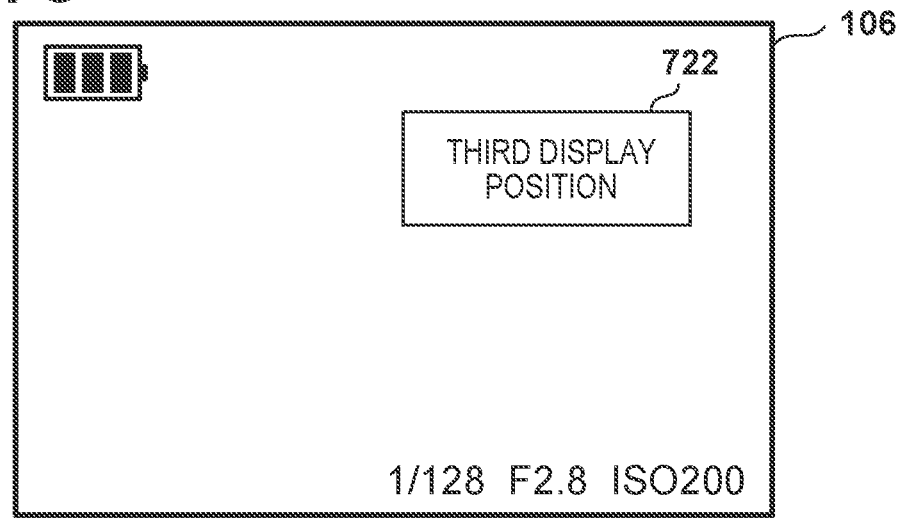

If it is determined that the patient information is to be displayed as (3i+3)th patient information after the image capture apparatus 1 is turned on ("YES" in step S606), the process proceeds to step S607. In step S607, the display control unit 107 then displays the patient information at a third display position 722 on the display unit 106 that is different from the first display position 720 and the second display position 721. FIG. 7C is a diagram illustrating one example of the third display position 722 on the display unit 106 at which the patient information is displayed.

If it is determined that the patient information is not to be displayed as (3i+3)th patient information after the image capture apparatus 1 is turned on ("NO" in step S606), the process proceeds to step S608. The control unit 150 then adds 1 to the counter variable i in step S608, and the process returns to step S602. Thereafter, the process from step S602 to step S608 is repeated until the patient information display position is determined. That is, after the image capture apparatus 1 is turned on, the first patient information is displayed at the first display position 720, the second patient information is displayed at the second display position 721, and the third patient information is displayed at the third display position 722. The fourth patient information is displayed at the first display position 720 again, and the display position is changed in order for the fifth patient information and onward. By changing the patient information display position, it is possible to grasp at a glance that patient information has been changed.

In this manner, according to the present embodiment, when an obtained image and information regarding a subject are recorded in association with each other, it is possible to prevent the subject and information from being erroneously associated with each other.

Other Embodiments

The present disclosure is not limited to the above-described embodiment, and various modifications can be made.

For example, the image capture apparatus 1 can further include a face authentication function. If acquired patient information is pre-registered in association with face image data of a patient, the image capture apparatus 1 collates the face image data with the face of a person appearing in the live view image, and upon determining that the patient is another person, issues a warning. For example, a case will be described as one example where, when the image capture apparatus 1 stores, in the memory, patient information regarding a person A that is pre-registered in association with face image data of the person A, and an image of a person B is obtained and is displayed as a live view image. In this case, the image capture apparatus 1 collates the face image data of the person A with the face of the person B, determines that the person B is another person, and issues a warning. Thus, the photographer can prevent the patient information regarding the person A from being erroneously recorded in association with the obtained image in which the person B appears.

While the above-described embodiment has been described assuming information that is recorded in association with obtained image data of a subject is patient information associated with a code, thumbnail image data of the code can also be recorded in association with the obtained image data of the subject.

While the above-described embodiment has been described assuming that the subject is a person, the subject does not necessarily have to be a person provided that a subject is associated with a code obtained in the information acquisition mode.

The above-described embodiment has been described assuming that the display unit 106 has three display positions at which patient information is displayed, but the number of patient information display positions is not necessarily three.

Embodiments can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiments and/or that includes one or more circuits (e.g., application specific integrated circuit (ASIC)) for performing the functions of one or more of the above-described embodiments, and by a method performed by the computer of the system or apparatus by, for example, reading out and executing the computer executable instructions from the storage medium to perform the functions of one or more of the above-described embodiments and/or controlling the one or more circuits to perform the functions of one or more of the above-described embodiments. The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present disclosure has been described with reference to exemplary embodiments, it is to be understood that the disclosure is not limited to the disclosed exemplary embodiments. The scope of the following claims is to be accorded the broadest interpretation so as to encompass all such modifications and equivalent structures and functions.

What is claimed is:

1. An image capture apparatus comprising:
   an image capture unit;
   a processor; and
   a memory storing a program which, when executed by the processor, causes the image capture apparatus to:
      obtain a first image by shooting a predetermined identifier using the image capture unit;
      obtain patient information corresponding to the predetermined identifier by reading the predetermined identifier from the first image;
      perform control to store the patient information in a predetermined memory area;
      perform control to display a second image obtained by shooting a subject as a patient using the image capture unit, as a live view image on a display unit;
      perform control to display and superimpose the stored patient information on the live view image on the display unit; and
      perform control to record a third image obtained by shooting a subject as a patient using the image capture unit in association with the stored patient information in a recording medium if a recording instruction is detected when the live view image is displaying on the display unit.

2. The image capture apparatus according to claim 1, wherein the patient information includes at least one of an identification number of a patient and a name of a patient,
   wherein at least one of the identification number of the patient and the name of the patient, as the patient information, is displayed and superimposed on the live view image on the display unit, and
   wherein at least one of the identification number of the patient and the name of the patient, as the patient information, is recorded and associated with the third image, in the recording medium.

3. The image capture apparatus according to claim 2, wherein the patient information which is displayed and superimposed on the live view image on the display unit is recorded and associated with the third image in the recording medium.

4. The image capture apparatus according to claim 1, wherein the program when executed by the processor further causes the image capture apparatus to analyze the predetermined identifier read from the first image, acquire character strings and search a database based on the character strings to obtain the patient information corresponding to the predetermined identifier.

5. The image capture apparatus according to claim 1, wherein the program when executed by the processor further causes the image capture apparatus to perform control to display a message on the display unit if the patient information corresponding to the predetermined identifier is not obtained.

6. The image capture apparatus according to claim 1, wherein the program when executed by the processor further causes the image capture apparatus to perform control to prohibit acceptance of an instruction based on a photographer's operation if the patient information corresponding to the predetermined identifier is not obtained.

7. The image capture apparatus according to claim 1, further comprising a shutter button,
   wherein the program when executed by the processor further causes the image capture apparatus to perform control to hide the patient information on the display unit if a half-pressing of the shutter button is detected and issue the recording instruction if a full-pressing of the shutter button is detected.

8. The image capture apparatus according to claim 1, wherein the program when executed by the processor further causes the image capture apparatus to perform control to hide the patient information if a predetermined time has elapsed after the patient information is displayed on the display unit.

9. The image capture apparatus according to claim 1, wherein the program when executed by the processor further causes the image capture apparatus to perform control to delete the patient information from the predetermine memory area.

10. The image capture apparatus according to claim 1, wherein the program when executed by the processor further causes the image capture apparatus to perform control to delete the patient information from the predetermine memory area when a power source is turned off.

11. The image capture apparatus according to claim 1, wherein the program when executed by the processor further causes the image capture apparatus to perform control to display the patient information stored in the predetermined memory area on the display unit if the patient information is stored in the predetermined memory area when a power source is turned on.

12. The image capture apparatus according to claim 1, wherein the program when executed by the processor further causes the image capture apparatus to
   obtain a first image newly by shooting a predetermined identifier using the image capture unit again after displaying and superimposing the patient information on the live view image on the display unit and before detecting the recording instruction,
   obtain patient information corresponding to the predetermined identifier newly again by reading the predetermined identifier from the first image obtained newly, and
   perform control to change the patient information which has been stored in the predetermined memory area into the patient information newly obtained.

13. The image capture apparatus according to claim 1, wherein the predetermined identifier is at least one of a one-dimensional code, a two-dimensional code and a figure pattern.

14. A method of controlling an image capture apparatus, the method comprising:
- obtaining a first image by shooting a predetermined identifier using the image capture unit;
- obtaining patient information corresponding to the predetermined identifier by reading the predetermined identifier from the first image;
- performing control to store the patient information in a predetermined memory area;
- performing control to display a second image obtained by shooting a subject as a patient using the image capture unit, as a live view image on a display unit;
- performing control to display and superimpose the stored patient information on the live view image on the display unit; and
- performing control to record a third image obtained by shooting a subject as a patient using the image capture unit in association with the stored patient information in a recording medium if a recording instruction is detected when the live view image is displaying on the display unit.

15. A non-transitory computer-readable storage medium storing a program that, when executed by a processor, causes the processor to perform operations comprising:
- obtaining a first image by shooting a predetermined identifier using the image capture unit;
- obtaining patient information corresponding to the predetermined identifier by reading the predetermined identifier from the first image;
- performing control to store the patient information in a predetermined memory area;
- performing control to display a second image obtained by shooting a subject as a patient using the image capture unit, as a live view image on a display unit;
- performing control to display and superimpose the stored patient information on the live view image on the display unit; and
- performing control to record a third image obtained by shooting a subject as a patient using the image capture unit in association with the stored patient information in a recording medium if a recording instruction is detected when the live view image is displaying on the display unit.

* * * * *